United States Patent
Kovi et al.

(10) Patent No.: US 10,519,121 B2
(45) Date of Patent: Dec. 31, 2019

(54) PROCESS AND NOVEL POLYMORPHIC FORM OF VORTIOXETINE AND ITS PHARMACEUTICALLY ACCEPTABLE SALTS

(71) Applicant: Apicore US LLC, Somerset, NJ (US)

(72) Inventors: Ravishanker Kovi, Monroe, NJ (US); Jayaraman Rao Kannapan, Vadodara (IN); Ananda Babu Thirunavakarasu, Gujarat (IN); Veerabhadra Rao Bobbili, Andhra Pradesh (IN); Gaurav Yadav, Utter Pradesh (IN)

(73) Assignee: Apicore US LLC, Canonsburg, PA (US)

( * ) Notice: Subject to any disclaimer, the term of this patent is extended or adjusted under 35 U.S.C. 154(b) by 0 days.

(21) Appl. No.: 15/854,458

(22) Filed: Dec. 26, 2017

(65) Prior Publication Data

US 2019/0002421 A1   Jan. 3, 2019

Related U.S. Application Data

(60) Provisional application No. 62/440,708, filed on Dec. 30, 2016.

(51) Int. Cl.
    *C07D 295/096*   (2006.01)
    *A61K 31/496*    (2006.01)

(52) U.S. Cl.
    CPC ........ *C07D 295/096* (2013.01); *A61K 31/496* (2013.01); *C07B 2200/13* (2013.01)

(58) Field of Classification Search
    CPC .................... C07D 295/096; A61K 31/496
    USPC ..................................... 544/336; 514/252.12
    See application file for complete search history.

(56) References Cited

U.S. PATENT DOCUMENTS

| | | | |
|---|---|---|---|
| 6,245,773 B1 | 6/2001 | Wong et al. | |
| 7,071,180 B2 | 7/2006 | Nilsson et al. | |
| 7,115,607 B2 | 10/2006 | Fotsch et al. | |
| 7,144,884 B2 | 12/2006 | Ruhland et al. | |
| 7,560,460 B2 | 7/2009 | Fotsch et al. | |
| 8,476,279 B2 | 7/2013 | Bang-Andersen | |
| 8,598,348 B2 | 12/2013 | Nicolajsen et al. | |
| 8,722,684 B2 | 5/2014 | Bang-Andersen et al. | |
| 8,940,746 B2 | 1/2015 | Treppendahl et al. | |
| 8,969,355 B2 | 3/2015 | Bang-Andersen et al. | |
| 9,090,575 B2 | 7/2015 | Ruhland et al. | |
| 9,095,588 B2 | 8/2015 | Faldt et al. | |
| 9,101,626 B2 | 8/2015 | Faldt et al. | |
| 9,125,908 B2 | 9/2015 | Bang-Andersen et al. | |
| 9,125,909 B2 | 9/2015 | Bang-Andersen et al. | |
| 9,125,910 B2 | 9/2015 | Bang-Andersen et al. | |
| 9,133,144 B2 | 9/2015 | Christensen | |
| 9,227,946 B2 | 1/2016 | Faldt et al. | |
| 9,353,073 B2 | 5/2016 | Ruhland et al. | |
| 9,499,504 B2 | 11/2016 | Hotter et al. | |
| 9,550,743 B2 | 1/2017 | Giannotti et al. | |
| 9,562,024 B2 | 2/2017 | Song et al. | |
| 9,687,484 B2 | 6/2017 | Giaffreda et al. | |
| 9,708,280 B2 | 7/2017 | Ruhland et al. | |
| 9,732,053 B2 | 8/2017 | Hotter et al. | |
| 9,861,630 B1 | 1/2018 | Faldt et al. | |
| 10,071,092 B2 * | 9/2018 | Jayaraman | A61K 31/495 |
| 2016/0015706 A1 | 1/2016 | Giaffreda et al. | |
| 2016/0083359 A1 | 3/2016 | Bang-Andersen et al. | |
| 2016/0200698 A1 | 7/2016 | Song et al. | |
| 2016/0214949 A1 | 7/2016 | Dwivedi et al. | |
| 2016/0289202 A1 | 10/2016 | Hotter et al. | |
| 2016/0368884 A1 | 12/2016 | de Diego et al. | |

FOREIGN PATENT DOCUMENTS

| | | | |
|---|---|---|---|
| WO | 2001007427 A1 | 2/2001 | |
| WO | 2003029232 A1 | 4/2003 | |
| WO | 2007144005 A1 | 12/2007 | |
| WO | 2010094285 A1 | 8/2010 | |
| WO | 2010121621 A1 | 10/2010 | |
| WO | 2013102573 A1 | 7/2013 | |
| WO | 2014044721 A1 | 3/2014 | |
| WO | 2014128207 A1 | 8/2014 | |
| WO | 2014177491 A1 | 11/2014 | |
| WO | 2014191548 A1 | 12/2014 | |
| WO | 2015044963 A1 | 4/2015 | |
| WO | 2015107057 A1 | 7/2015 | |
| WO | 2015114395 A1 | 8/2015 | |
| WO | 2015166379 A1 | 11/2015 | |
| WO | 2015166379 A2 | 11/2015 | |
| WO | 2015114395 A1 | 12/2015 | |
| WO | 2016062860 A1 | 4/2016 | |
| WO | 2016079751 A2 | 5/2016 | |
| WO | 2016116077 A1 | 7/2016 | |
| WO | 2016125191 A2 | 8/2016 | |
| WO | 2016125190 A2 | 9/2016 | |
| WO | 2016125191 A3 | 9/2016 | |
| WO | 2016135636 A1 | 9/2016 | |
| WO | 2016151328 A1 | 9/2016 | |
| WO | 2017125504 A1 | 7/2017 | |
| WO | 2017137048 A1 | 8/2017 | |
| WO | 2017154016 A1 | 9/2017 | |
| WO | 2017162536 A1 | 9/2017 | |

* cited by examiner

*Primary Examiner* — Venkataraman Balasubramanian

(57) ABSTRACT

Processes are disclosed for making vortioxetine and pharmaceutically acceptable salts thereof. A propylene glycol solvate of vortioxetine hydrobromide is disclosed. A novel crystalline form of vortioxetine hydrobromide propylene glycol solvate, designated form AC1, is disclosed along with a method for making same. Form AC1 may be characterized by an x-ray powder diffraction pattern with peaks at about 19.64, 22.85, 25.51, 29.57, 30.18±0.2 degrees 2-theta.

4 Claims, 3 Drawing Sheets

PROCESS AND NOVEL POLYMORPHIC FORM OF VORTIOXETINE AND ITS PHARMACEUTICALLY ACCEPTABLE SALTS

CROSS-REFERENCE TO RELATED APPLICATIONS

This non-provisional application claims the benefit of U.S. Provisional Patent Application No. 62/440,708 filed Dec. 30, 2016, the entirety of which is incorporated herein by reference.

FIELD OF THE INVENTION

The present invention relates to vortioxetine. Specifically, the present invention relates to an improved process for the preparation of vortioxetine of Formula I and its pharmaceutically acceptable salts, and a novel crystalline form of vortioxetine hydrobromide propylene glycol solvate.

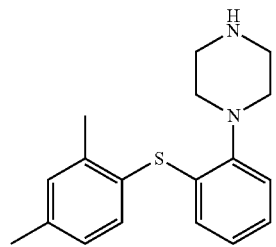

Formula I

BACKGROUND OF THE INVENTION

Vortioxetine hydrobromide is marketed by Takeda Pharmaceuticals under the trade name TRINTELLIX®. Vortioxetine hydrobromide is indicated for the treatment of major depressive disorder (MDD). It is a serotonin (5-HT) reuptake inhibitor, which is considered as its mechanism of action for the treatment of MDD.

SUMMARY OF THE INVENTION

International application numbers WO2003029232, WO2007144005, WO02013102573, WO2014128207, and WO2014191548 disclose various processes for the preparation of vortioxetine.

Although several processes have been reported in the prior art for the preparation of vortioxetine, they suffer from one or more drawbacks such as involving the use of hazardous reagents, costly reagents, and extensive protection and deprotection steps. Hence, there is an ongoing need for simple, cost-effective, and industrially viable processes for the production of vortioxetine and its pharmaceutically acceptable salts. International application WO 2007144005 discloses crystalline vortioxetine in its free-base form as well as crystalline vortioxetine salts such as hydrochloride, mesylate, fumarate, maleate, meso-tartrate, L-(+)-tartrate, D-(−)-tartrate, sulfate, phosphate, and nitrate.

International application WO 2010094285 discloses an isopropanol solvate of vortioxetine hydrobromide as well as a process for the purification of vortioxetine hydrobromide.

International application WO 2010121621 discloses crystalline forms of vortioxetine L-lactate and vortioxetine DL-lactate.

International application WO 2014044721 discloses vortioxetine hydrobromide form delta and a vortioxetine hydrobromide hydrate.

International application WO 2014177491 discloses amorphous vortioxetine hydrobromide in association with an adsorbent.

International application WO 2015044963 discloses amorphous vortioxetine hydrobromide and a solid dispersion of vortioxetine free base or salts thereof and a polymer.

International application WO2015114395 discloses vortioxetine salts such as succinate, salicylate, monocitrate monohydrate, monocitrate anhydrate, malonate, hemioxalate, L-malate, benzene sulfonate, acetate, L-(+)-mandelate, hemicitarte, and monooxalate.

International application WO2015166379 discloses vortioxetine HBr Form A, Form Ad, Form B & Form C, vortioxetine adipate, vortioxetine malonate, vortioxetine glutarate, vortioxetine HBr diethyl ether solvate, amorphous form of vortioxetine HBr, and co-precipitate of vortioxetine HBr.

U.S. Published Patent Application 2016/0015706A1 discloses vortioxetine HBr lamda, omega and sigma.

International application WO2016/125191 discloses amorphous premix vortioxetine hydrobromide and also crystalline forms of M1, M2, M3, M4 of vortioxetine hydrobromide.

International application WO2016135636 A1 discloses crystalline forms of vortioxetine hydrobromide.

The discovery of new polymorphic forms and/or solvates of a drug or a pharmaceutically useful compound provide opportunity to improve the characteristics of a pharmaceutically acceptable dosage form of the drug with a targeted release profile or other desired characteristics.

Despite the aforementioned disclosures mentioning various polymorphic forms, there is a need for a new polymorphic form of vortioxetine hydrobromide and processes for preparation thereof.

There remains a need for further improvement in properties of solid vortioxetine hydrobromide, such as stability, purity, flowability, vapor impermeability, solubility, and bioavailability.

In accordance with certain embodiments the subject matter of the present invention includes a novel crystalline polymorphic form of vortioxetine hydrobromide, namely, vortioxetine hydrobromide propylene glycol solvate, designated form AC1.

In one aspect of the present invention there is provided a process of preparation of vortioxetine of formula I or pharmaceutically acceptable salts thereof including the steps of:

a. reaction of 1-chloro-2-nitrobenzene (Formula VII) with piperazine in the presence of suitable solvent and suitable reaction conditions to afford 1-(2-nitrophenyl) piperazine of Formula VI;

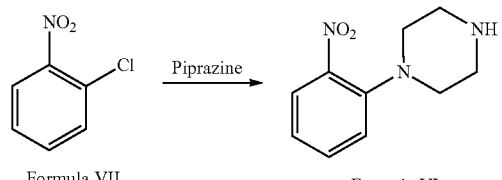

b. reaction of 1-(2-nitrophenyl)piperazine of (Formula VI) with benzyl chloride in the presence of suitable solvent and suitable reaction conditions to afford 1-benzyl-4-(2-nitrophenyl)piperazine of Formula V;

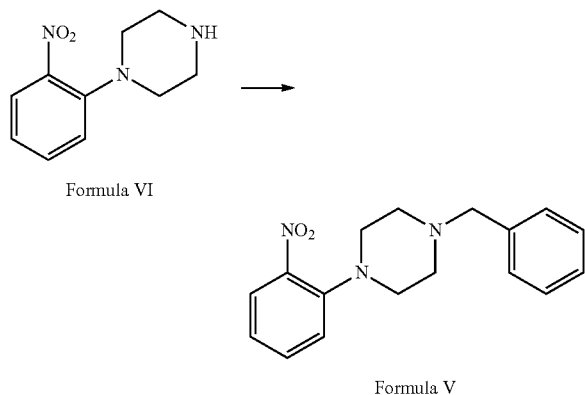

Formula VI

Formula V c. reduction of 1-benzyl-4-(2-nitrophenyl)piperazine of Formula V in the presence of suitable reducing agent and suitable reaction conditions to afford the 2-(4-benzylpiperazin-1-yl)aniline Formula IV;

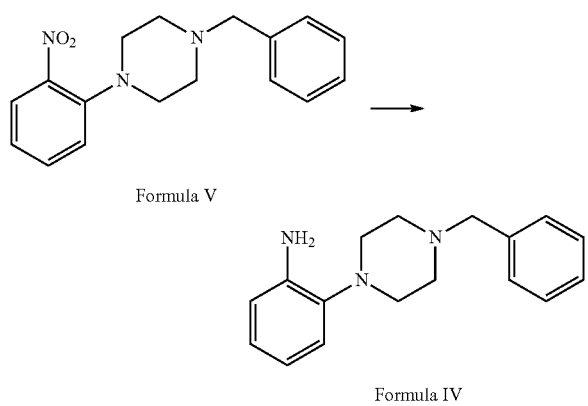

Formula V

Formula IV d. reaction of 2-(4-benzylpiperazin-1-yl)aniline with potassium methylxanthate in the presence of suitable reagent and solvent to afford S-(2-(4-benzylpiperazin-1-yl)phenyl)O-ethyl carbonodithioate of Formula III;

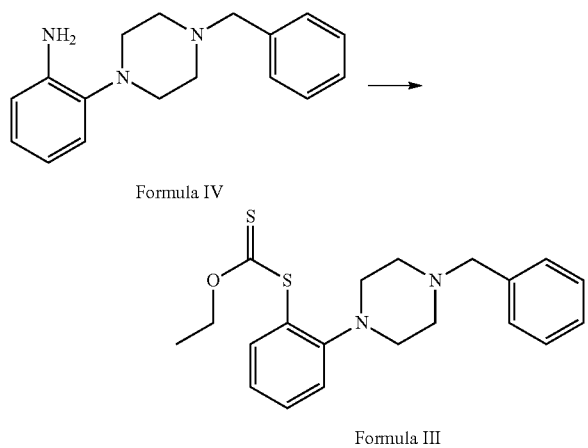

Formula IV

Formula III e. condensation of S-(2-(4-benzylpiperazin-1-yl)phenyl)O-ethyl carbonodithioate with 2,4-dimethyliodobenzene in the presence of copper acetate and ethylenediamine to afford 1-benzyl-4-(2-(2,4-dimethyl phenyl) thio)phenyl) piperazine of Formula II;

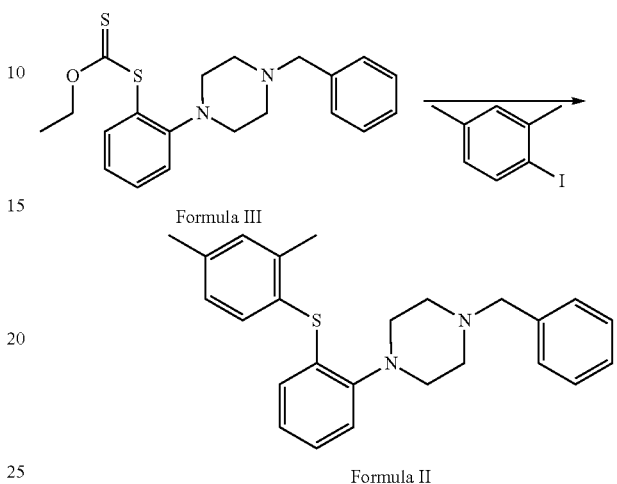

Formula III

Formula II f. deprotection of 1-benzyl-4-(2-(2,4-dimethylphenyl)thio)phenyl)piperazine in the presence of 1-chloroethylchloroformate and suitable solvent to afford vortioxetine free base of Formula I. The vortioxetine free base may be further reacted with an acid, such as but not limited to hydrobromic acid, to obtain a pharmaceutically acceptable salt of Formula I, such as but not limited to vortioxetine hydrobromide.

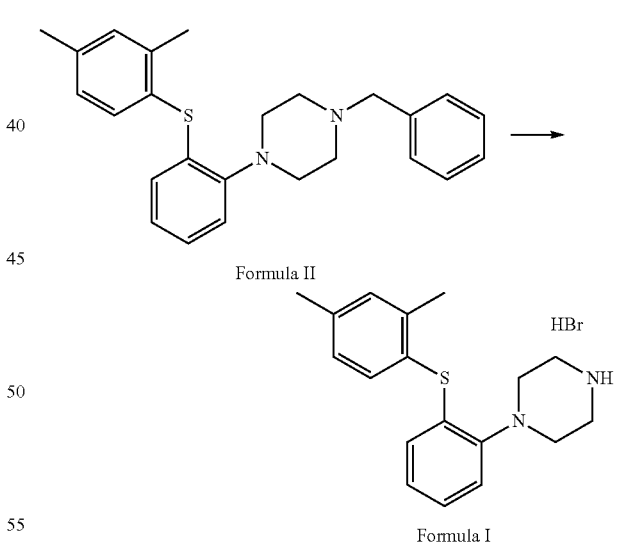

Formula II

Formula I

In another embodiment, the present disclosure encompasses a process for preparing vortioxetine hydrobromide propylene glycol solvate form AC1 including the steps of:
a. obtaining a solution of propylene glycol and vortioxetine hydrobromide by combining vortioxetine hydrobromide and propylene glycol;
b. maintaining the solution of step a) at a temperature of about 0° C. to about 150° C.; and
c. isolating crystalline vortioxetine hydrobromide propylene glycol solvate form AC1 from the solution.

In an embodiment, the present disclosure provides crystalline vortioxetine hydrobromide propylene glycol solvate, designated as form AC1, characterized by data selected from: an x-ray powder diffraction pattern with peaks at about 19.82, 20.97, 23.06, 25.7, 29.77±0.2 degrees 2-theta; an x-ray powder diffraction pattern with peaks substantially as depicted in FIG. 1; and combinations thereof.

In an embodiment, the present disclosure provides crystalline vortioxetine hydrobromide propylene glycol solvate, designated as form AC1, which can be characterized by an x-ray powder diffraction patter with peaks at about 19.64, 22.85, 25.51, 29.57, 30.18±0.2 degrees 2-theta.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE INVENTION

Figure 1:
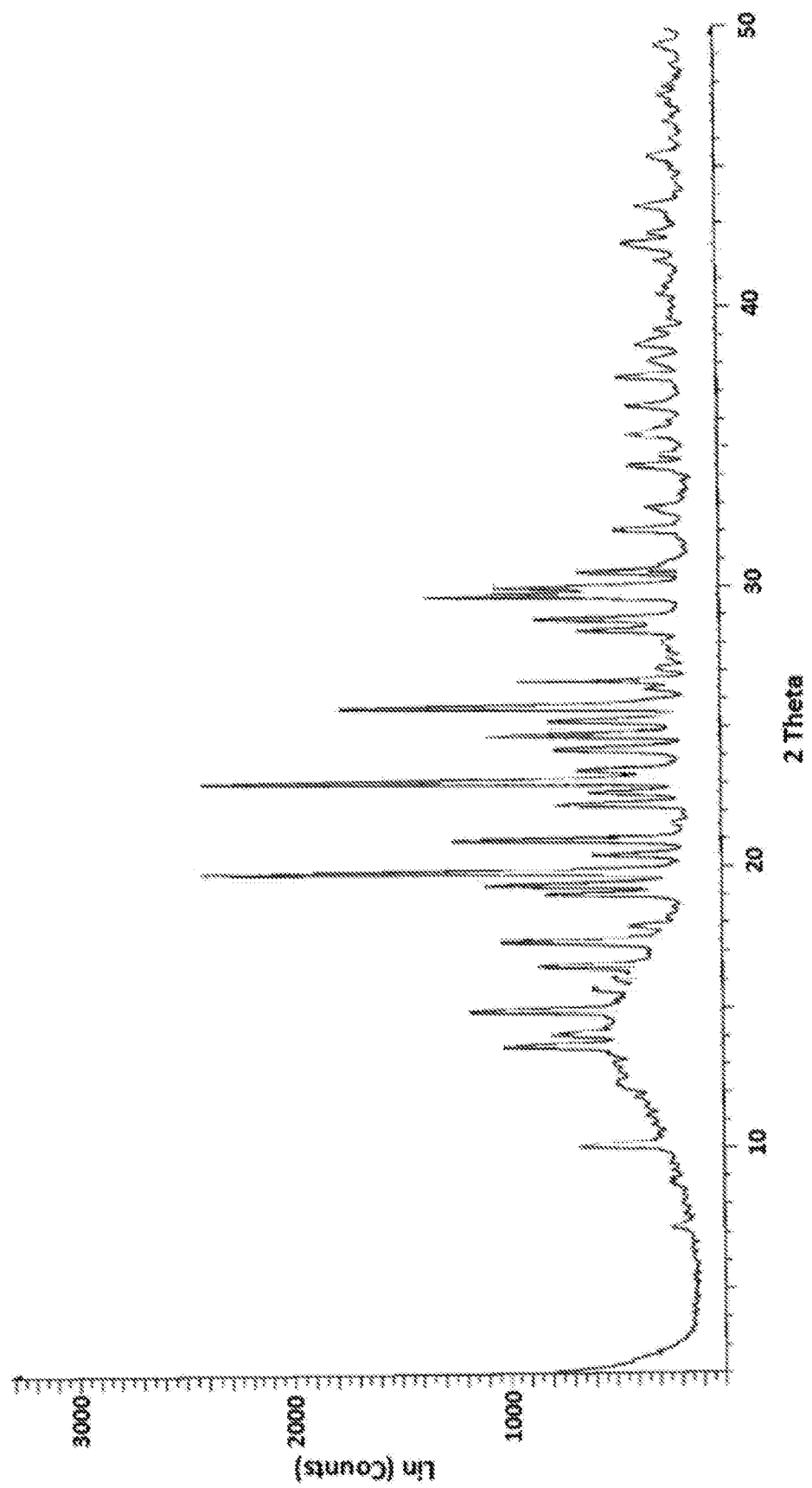
FIG. 1 is a graphical depiction of an X-ray powder diffraction pattern of vortioxetine hydrobromide propylene glycol solvate form AC1 according to an embodiment of the present disclosure.

Embodiments of the present invention now will be described more fully hereinafter with reference to the accompanying examples and experiments, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All percentages and ratios used herein are by weight of the total composition and all measurements made are at 25° C. and normal pressure unless otherwise designated. All temperatures are in degrees Celsius unless specified otherwise. In some embodiments.

As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values.

In one aspect of the present invention there is provided a process of preparation of vortioxetine of Formula I including the steps of:

a. reacting 1-chloro-2-nitrobenzene (Formula VII) with piperazine in the presence of suitable solvent and suitable reaction conditions to afford 1-(2-nitrophenyl) piperazine of Formula VI:

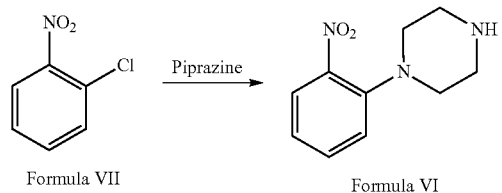 [SMILES: O=[N+]([O-])c1ccccc1Cl ; O=[N+]([O-])c1ccccc1N1CCNCC1]

b. reacting 1-(2-nitrophenyl)piperazine of Formula VI with benzyl chloride in the presence of suitable solvent and suitable reaction conditions to afford 1-benzyl-4-(2-nitrophenyl)piperazine of Formula V;

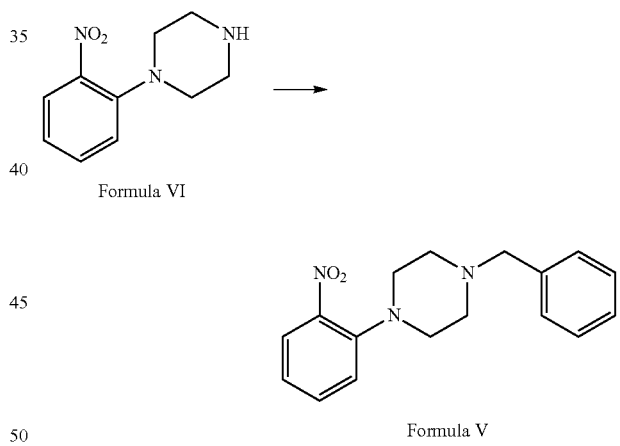

c. reducing 1-benzyl-4-(2-nitrophenyl)piperazine of Formula V in the presence of suitable reducing agent and suitable reaction conditions to afford the 2-(4-benzylpiperazin-1-yl)aniline Formula IV;

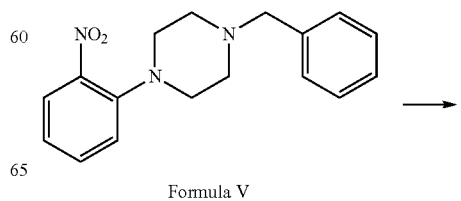

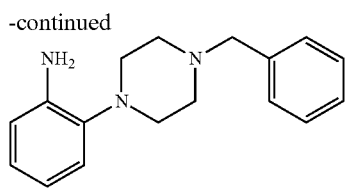

Formula IV d. reacting 2-(4-benzylpiperazin-1-yl)aniline with potassium methylxanthate in the presence of suitable reagent and solvent to afford S-(2-(4-benzylpiperazin-1-yl)phenyl)O-ethyl carbonodithioate of Formula III;

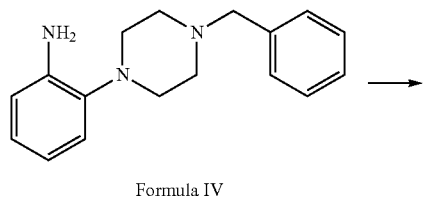

Formula IV

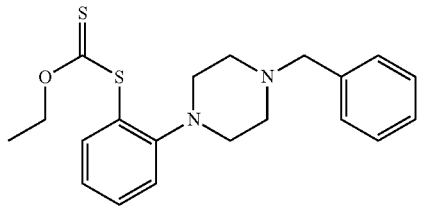

Formula III e. condensing S-(2-(4-benzylpiperazin-1-yl)phenyl)O-ethyl carbonodithioate with 2,4-dimethyliodobenzene in the presence of copper acetate and ethylenediamine to afford 1-benzyl-4-(2-(2,4-dimethyl phenyl) thio)phenyl) piperazine of Formula II;

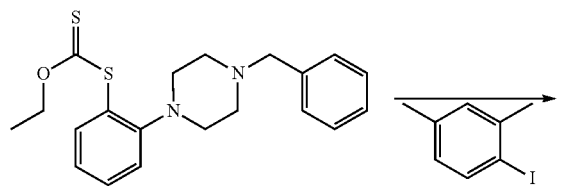

Formula III

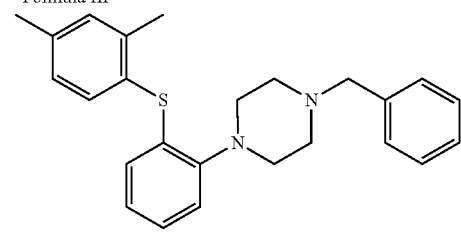

Formula II f. deprotecting the 1-benzyl-4-(2-(2,4-dimethylphenyl)thio) phenyl)piperazine in the presence of 1-chloroethylchloroformate and suitable solvent to afford vortioxetine free base of Formula I. The vortioxetine free base may be further reacted with an acid such as but to limited to hydrobromic acid to obtain a pharmaceutically acceptable salt of vortioxetine of Formula I such as but not limited to vortioxetine hydrobromide.

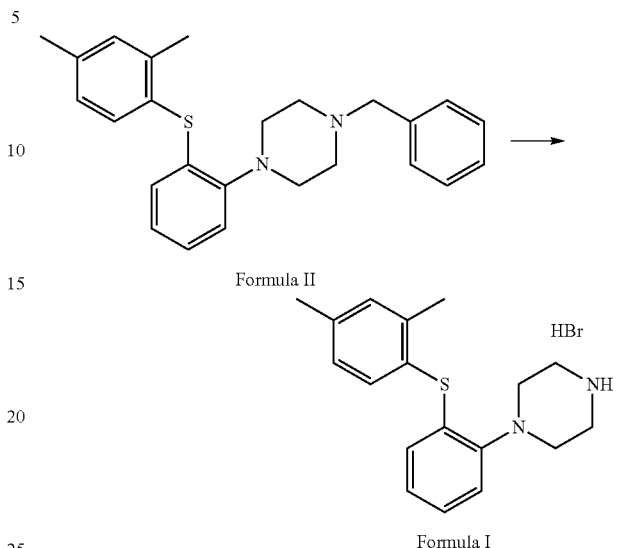

Step (a) involves reaction of 1-chloro-2-nitrobenze (Formula VII) with piperazine in the presence of suitable solvent and suitable reaction conditions to afford 1-(2-nitrophenyl) piperazine of Formula VI.

Suitable solvents that may be used include but are not limited to alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of step (a) may be less than about 150° C., or less than about 120° C., or less than about 80° C., or less than about 60° C., or any other suitable temperatures.

The reaction may be carried out for any desired time period ranging from about 30 minutes to about 10 hours or longer.

Step (b) involves reaction of 1-(2-nitrophenyl) piperazine of Formula VI with benzyl chloride in the presence of suitable solvent and base in suitable reaction conditions to afford 1-benzyl-4-(2-nitrophenyl) piperazine of Formula V.

Suitable bases that may be used for this reaction include but are not limited to inorganic bases, such as, for example, sodium hydroxide, potassium hydroxide, sodium methoxide, potassium teritarybutoxide, sodium teritarybutoxide, sodium carbonate, potassium carbonate, sodium bicarbonate, potassium bicarbonate, and the like, either alone or as their aqueous solutions; organic bases, such as, for example, triethylamine, pyridine, N-methyl morpholine, diisopropyl amine, diisopropyl ethylamine, and the like; or mixtures thereof.

Suitable solvents that may be used include but are not limited to alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of step (b) may be less than about 150° C., or less than about 120° C., or less than about 80° C., or less than about 60° C., or any other suitable temperatures.

The reaction may be carried out for any desired time period ranging from about 30 minutes to about 10 hours or longer.

Step (c) involves reduction of 1-benzyl-4-(2-nitrophenyl) piperazine of Formula V in the presence of suitable reducing agent and suitable reaction conditions to afford the 2-(4-benzylpiperazin-1-yl) aniline Formula IV.

Suitable reducing agents that may be used in the reaction include but are not limited to borane complexes, metals such as iron, tin, zinc; transition metals such as palladium-carbon, platinum oxide, Raney nickel in presence of hydrogen or a hydrogen source selected from ammonium formate, sodium dihydrogen phosphate, hydrazine, for example, Fe—NH$_4$Cl, Fe—HCl, Fe—CaCl$_2$, Sn—HCl, NaHS, Zn—AcOH, Pd/C—H$_2$, hydrazine hydrate-Raney Ni, NaBH4-NiCl$_2$.6H$_2$O, Ni(OAc)2.4H$_2$O, CoCl$_2$ and like metals.

A suitable temperature for the reaction of step (c) may be less than about 150° C., or less than about 120° C., or less than about 80° C., or less than about 60° C., or any other suitable temperatures.

The reaction may be carried out for any desired time period ranging from about 30 minutes to about 10 hours or longer.

Step (d) involves reaction of 2-(4-benzylpiperazin-1-yl) aniline with potassium methyl xanthate in the presence of a suitable solvent to afford S-(2-(4-benzylpiperazin-1-yl)phenyl)O-ethyl carbonodithioate of Formula III.

Suitable solvents that may be used include and are not limited to alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of step (d) may be less than about 150° C., or less than about 120° C., or less than about 80° C., or less than about 60° C., or any other suitable temperatures.

The reaction may be carried out for any desired time period ranging from about 30 minutes to about 10 hours or longer.

Step (e) involves condensation of S-(2-(4-benzylpiperazin-1-yl)phenyl)O-ethyl carbonodithioate with 2,4-dimethyliodobenzene in the presence of copper acetate and ethylenediamine to afford 1-benzyl-4-(2-(2,4-dimethyl phenyl) thio)phenyl) piperazine of Formula II.

A suitable temperature for the reaction of step (e) may be less than about 150° C., or less than about 120° C., or less than about 80° C., or less than about 60° C., or any other suitable temperatures.

The reaction may be carried out for any desired time period ranging from about 30 minutes to about 10 hours or longer Step (f) involves deprotection of 1-benzyl-4-(2-(2,4-dimethyl phenyl)thio) phenyl) piperazine in the presence of 1-chloroethylchloroformate and suitable solvent to afford vortioxetine free base of Formula I which may be further reacted with a salt such as but not limited to hydrobromic acid to obtain a pharmaceutically acceptable salt of Formula I such as but not limited to vortioxetine hydrobromide.

Suitable solvents that may be used include but are not limited to alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water or mixtures thereof.

A suitable temperature for the reaction of Step (f) may be less than about 150° C., or less than about 120° C., or less than about 80° C., or less than about 60° C., or any other suitable temperatures.

The reaction may be carried out for any desired time period ranging from about 30 minutes to about 10 hours or longer.

In another embodiment, the present application encompasses a process for preparing vortioxetine hydrobromide propylene glycol solvate form AC1 including the steps of:
a. obtaining a solution of vortioxetine hydrobromide in propylene glycol solvent;
b. maintaining the solution of step a) at a temperature of about 0° C. to about 150° C.; and
c. isolating crystalline vortioxetine hydrobromide propylene glycol solvate form AC1 from the solution.

Obtaining a solution according to step a) includes dissolving vortioxetine hydrobromide in propylene glycol solvent or obtaining a solution of vortioxetine hydrobromide in propylene glycol as a final step in the preparation of the compound. Vortioxetine hydrobromide employed in this step may be obtained by any process known in the art as well as the processes disclosed herein and is not confined to processes disclosed herein.

The solution of step a) may be provided at any temperature ranging from about 0° C. to about reflux temperature of the solvent, preferably at about 50° C. to about 150° C., more preferably at about 100° C. to about 150° C., most preferably at about 100° C. to about 135° C.

The solution may optionally be treated with activated charcoal and then filtered to remove the carbon. The solution may optionally be filtered by passing through paper, glass fiber, or other membrane material, or a bed of a clarifying agent such as Celite®. Depending upon the equipment used, as well as the concentration and temperature of the solution, the filtration apparatus may need to be heated or cooled to avoid undesired crystallization.

Step b) involves maintaining the solution of step b) at a temperature of about 0° C. to about 150° C.

In one embodiment the solution of step b) is maintained at a temperature of about 0° C. to about 150° C. for sufficient time. Sufficient time as disclosed herein is the time required to ensure the formation of crystalline vortioxetine hydrobromide. In an embodiment, the reaction mixture is maintained for a time period of about 30 minutes to about 50 hours.

In other embodiments, the solution of step b) is maintained at a temperature of about 10° C. to about 40° C., more preferably at about 25° C. to about 35° C.

Step c) involves isolating vortioxetine hydrobromide propylene glycol solvate Form AC1 from the solution of step b). The crystalline vortioxetine hydrobromide propylene glycol solvate form AC1 is isolated in a manner known per se, and depending on the solvent used, which include but are not limited to filtration by gravity or by suction/vacuum, distillation, centrifugation, or slow evaporation or the like. In an embodiment, vortioxetine hydrobromide propylene glycol solvate form AC1 may be isolated by filtration under vacuum and suction drying at a temperature of about 25° C. to about 35° C.

Drying the crystalline vortioxetine hydrobromide propylene glycol solvate form AC1 may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 70° C., at a temperature of about 60° C., at a temperature of about 40° C. or at a temperature of about 30° C. The drying may be carried out for any time periods required for obtaining a desired quality, such as from about 15 minutes to several hours, or longer.

The crystalline form of vortioxetine hydrobromide propylene glycol solvate designated as form AC1 has advantageous properties selected from at least one of chemical purity, stability—such as storage stability, stability to dehydrate, stability to polymorphic conversion, flowability, solubility, morphology or crystal habit, low hygroscopicity and low content of residual solvents.

Figure 2:
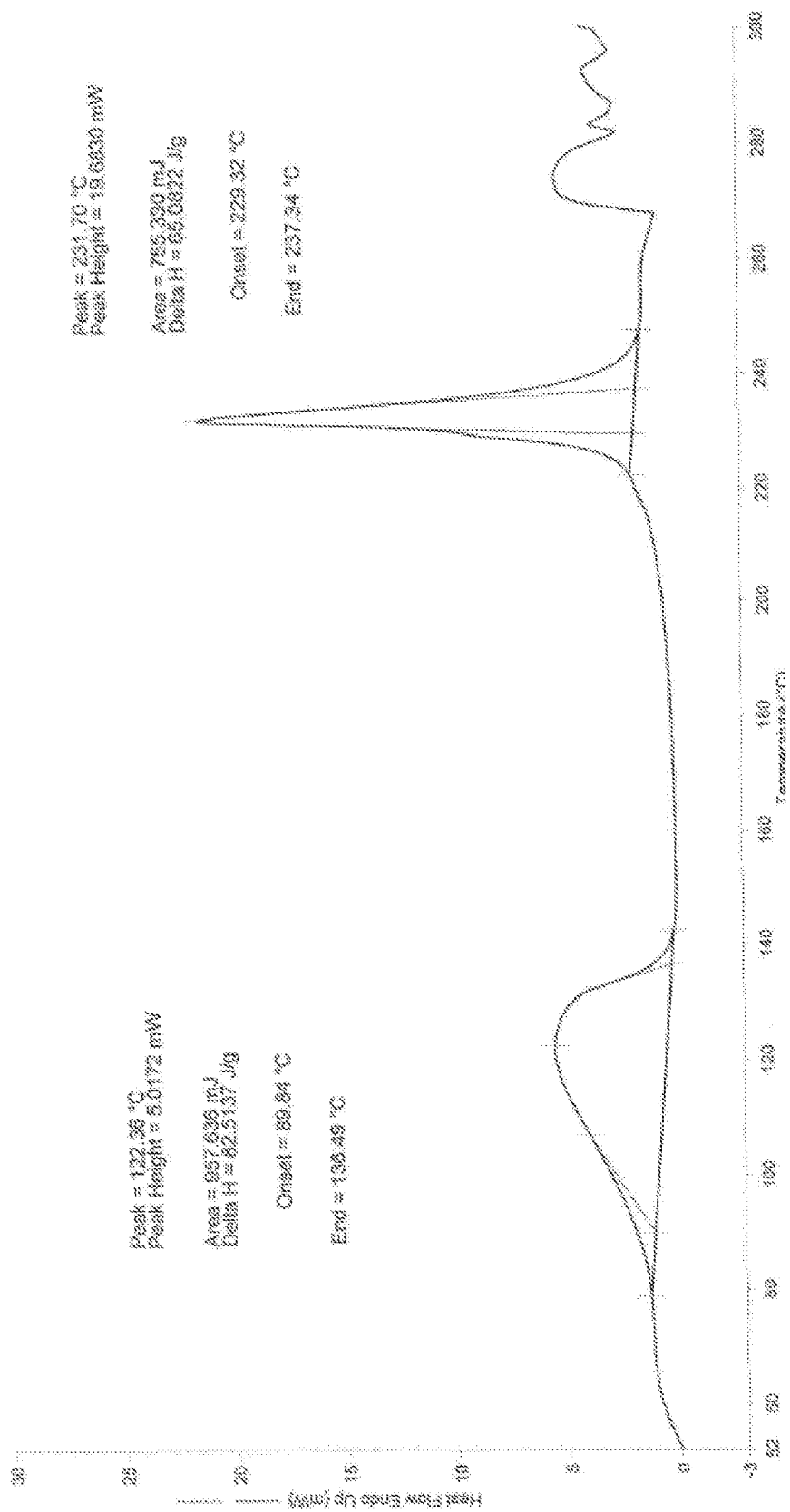
FIG. 2 is a graphical depiction of a DSC thermogram of vortioxetine hydrobromide propylene glycol solvate form AC1 according to an embodiment of the present disclosure.

FIG. 1 shows an X-ray powder diffraction pattern of vortioxetine hydrobromide propylene glycol solvate form AC1 having peaks at 7.130; 10.051; 13.619; 14.041; 14.894; 15.655; 16.083; 16.448; 17.328; 17.828; 18.982; 19.317; 19.816; 20.395; 20.969; 21.529; 22.209; 22.639; 23.055; 23.447; 23.718; 24.198; 24.707; 25.177; 25.704; 26.373; 26.626; 27.082; 27.461; 27.996; 28.418; 28.839; 29.722; 29.991; 30.539; 32.059; 32.696; 32.866; 34.330; 34.723; 35.446; 35.679; 35.955; 36.499; 37.512; 38.099; 38.674; 39.195; 39.628; 40.494; 41.657; 42.277; 42.648; 43.619; 44.582; 45.406; 46.034; 46.663; 47.298; 47.605; 47.923; 48.645; and 49.379 degrees 2-theta. Table 1 lists characteristic peaks of vortioxetine hydrobromide propylene glycol solvate form AC1 as shown in FIG. 1 made in one example according to the present disclosure. FIG. 2 is a graphical depiction of a DSC thermogram of vortioxetine hydrobromide propylene glycol solvate form AC1 made according to the present disclosure.

TABLE 1

| 2 theta |
| --- |
| 16.448 |
| 17.328 |
| 19.317 |
| 19.816 |
| 20.969 |
| 23.055 |
| 24.707 |
| 25.704 |
| 28.839 |
| 29.722 |
| 29.991 |

Crystalline vortioxetine hydrobromide propylene glycol solvate form AC1 may thus be characterized by data selected from an x-ray powder diffraction pattern with peaks at about 19.82, 20.97, 23.06, 25.7, 29.72±0.2 degrees 2-theta; an x-ray powder diffraction pattern with peaks substantially as depicted in FIG. 1; and combinations thereof.

Figure 3:
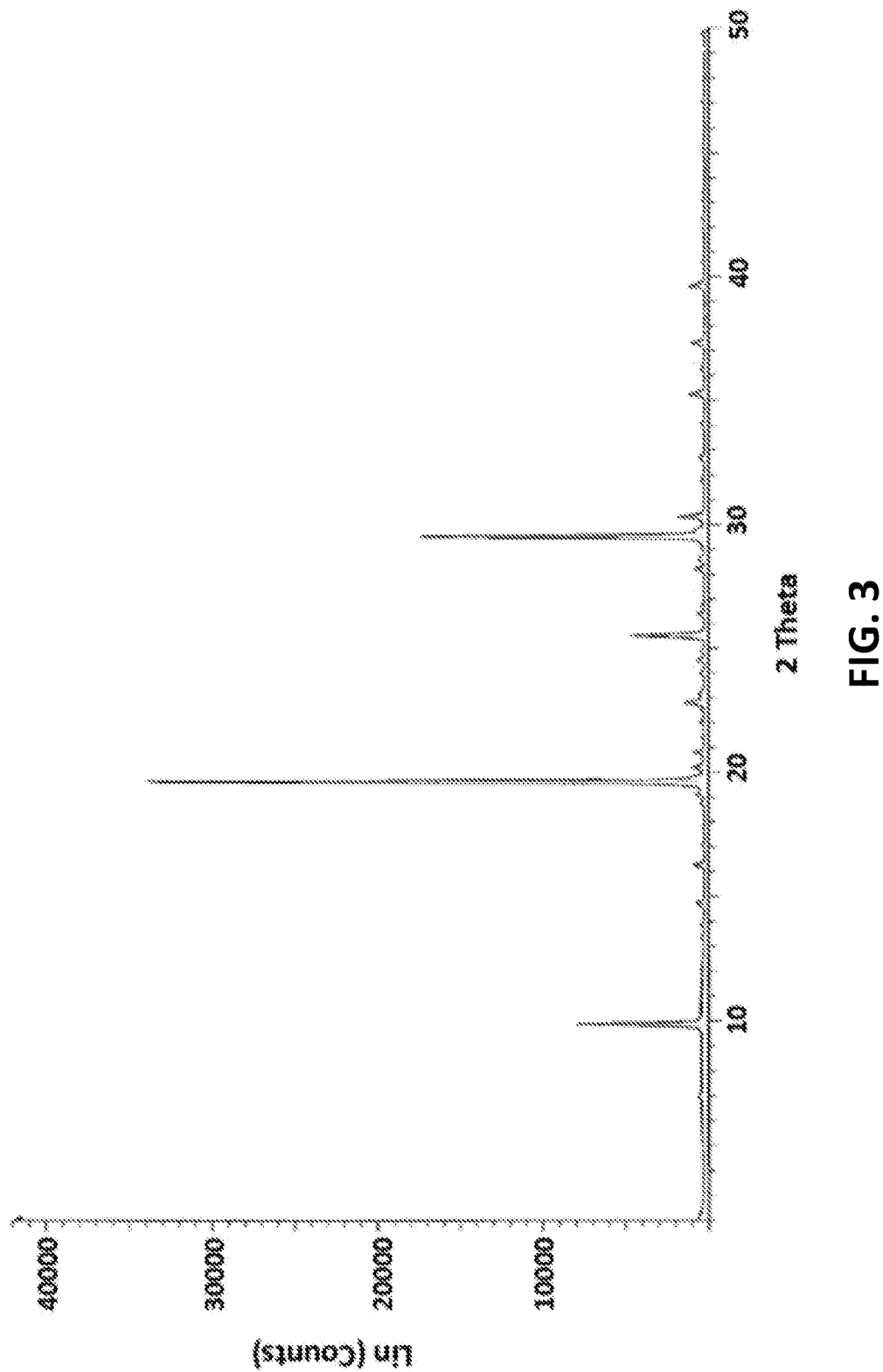
FIG. 3 is a graphical depiction of an X-ray powder diffraction pattern of vortioxetine hydrobromide propylene glycol solvate form AC1 according to an embodiment of the present disclosure.

FIG. 3 shows an X-ray powder diffraction pattern of vortioxetine hydrobromide propylene glycol solvate form AC1 having peaks at 6.926; 8.527; 9.848; 12.011; 13.321; 13.837; 14.676; 15.805; 16.250; 17.068; 17.695; 18.772; 19.109; 19.635; 20.211; 20.800; 21.365; 22.003; 22.472; 22.796; 23.150; 23.976; 24.487; 24.891; 25.490; 26.378; 26.777; 27.216; 28.227; 28.622; 29.508; 30.341; 31.777; 32.683; 34.098; 34.630; 35.266; 36.320; 37.354; 37.738; 38.388; 38.907; 39.651; 40.596; 41.357; 42.052; 42.424; 43.111; 43.490; 44.771; 45.153; 46.424; 47.074; 47.122; 47.715; 46.013; 46.542; 49.113; and 49.834 degrees 2-theta. Table 2 contains data for vortioxetine hydrobromide propylene glycol solvate form AC1 as shown in FIG. 3 made according to one example of the present disclosure.

TABLE 2

| 2θ (deg) |
| --- |
| 16.2504 |
| 19.1087 |
| 19.6355 |
| 20.2107 |
| 20.8000 |
| 22.7961 |
| 24.4873 |
| 25.4895 |
| 26.3781 |
| 28.2267 |
| 28.6222 |
| 29.5083 |
| 30.3409 |
| 32.6827 |
| 35.2659 |
| 37.3543 |
| 39.6513 |

Experimentation and analysis revealed vortioxetine hydrobromide propylene glycol solvate form AC1, produced from a solution of vortioxetine hydrobromide in propylene glycol, may be characterized by an x-ray powder diffraction pattern with peaks at about 19.64, 22.85, 25.51, 29.57, 30.18±0.2 degrees 2-theta.

Certain specific aspects and embodiments of the present application will be explained in more detail with reference to the following examples, which are provided only for purposes of illustration and should not be construed as limiting the scope of the present application in any manner.

EXAMPLES

In the following examples, in cases in which a specific value is listed and followed by a range of values, the specific value is the measured value and the range of values is the target range that may be employed.

Example 1: Preparation of 1-(2-nitrophenyl) piperazine

To a solution of piperazine (224.0 gm) dissolved in methanol (600.0 ml) under an atmosphere of nitrogen, 1-chloro-2-nitrobenzene (100.0 gm) was slowly added while the temperature was maintained at 30° C. The temperature of the reaction mass was raised to 70° C. (70-100° C.) and the contents maintained at this temperature for 24 hours (20-24 hours). After the reaction was complete the reaction solution was distilled under vacuum below 50° C. Charged water (600 ml) and toluene (600 ml) into the crude. The pH of the reaction mass was adjusted to below 1.0 with hydrochloric acid. The organic layer and aqueous layer were separated. The aqueous layer was taken and the reaction mass pH was adjusted to 7.0-8.0 with sodium carbonate solution. The obtained aqueous layers were extracted with dichloromethane (300 ml and 150 ml), and the organic layer dried with sodium sulphate. The organic layers were collected and concentrated under reduced pressure at 45° C. to furnish the title compound (120.0 gm) as brown viscous oil which was used for the next step without further purification.

Example 2: Preparation of 1-benzyl-4-(2-nitrophenyl) piperazine 1-(2-nitrophenyl) piperazine (100.0 gm) was dissolved in DMF (200.0 ml) and toluene (500 ml) at room temperature. The contents were cooled to 0° C. followed by addition of potassium carbonate (160.0 gm) and benzyl chloride (73.0 gm) while maintaining the temperature at 0° C. The temperature was raised to 100° C. (100-120° C.) and the reaction mixture maintained at this temperature for 2 hours (2-4 hours). On completion of the reaction (monitored by TLC), the contents were brought to room temperature and slowly poured into ice water (1000 ml) with vigorous stirring. The organic layer was washed successively with water (2×400 ml), brine (400 ml), dried over anhydrous sodium sulphate and solvent removed under reduced pressure to furnish the title compound (140 gm) as thick orange oil. The product was used for the next step without further purification.

Example 3: Preparation of 2-(4-benzylpiperazin-1-yl) aniline

A solution of 1-benzyl-4-(2-nitrophenyl) piperazine (100.0 gm) in hydrochloric acid (400.0 ml) at 30° C. was prepared. Stannous chloride (227.8 gm) was successively added, and the contents were allowed to warm to temperature of 60-65° over 1 hours (1-2 hours) while the stirring continued. On completion of reaction, the contents were brought to room temperature and slowly poured into ice water (2000 ml) with vigorous stirring. The reaction mass pH was adjusted to 12.0-14.0 with sodium hydroxide solution. The mixture was extracted with ethyl acetate (3×3000 ml) and the organic layer separated and washed successively with water (2×300 ml), brine (300 ml) and dried over anhydrous sodium sulphate. Solvent was removed under reduced pressure and isolated in isopropyl ether and hexane (1:3) to obtain the desired amine (45.0 gm) as a solid which was used for the next step without further purification.

Example 4: Preparation of 1-(2-((2,4-dimethylphenyl) thio) phenyl) piperazine HCl 2-(4-benzylpiperazin-1-yl) aniline (100.0 gm) was dissolved in acetonitrile (500 ml) and the contents cooled to 0° C. p-toluene sulfonic acid (213.7 gm) was added followed by stirring at 0° C. for 10 minutes. Sodium nitrite (51.6 gm) was added followed by potassium ethyl xanthate (60.0 gm) solution in water over a period of 30 minutes while maintaining the temperature at 0° C. (0-5° C.). On completion of reaction, the mixture was poured into water (1200 ml) with vigorous stirring. The contents were extracted with ethyl acetate (2×350 ml) and the organic layer washed with water (2×500 ml), brine (500 ml) and dried over anhydrous sodium sulfate. The organic layer was treated with carbon, solvent was removed under reduced pressure to furnish the crude xanthenes (130.0 gm). The obtained crude xanthenes (130.0 gm) and 2, 4-dimethyl iodobenzene (67.2 gm) were dissolved in dry DMF (650.0 ml). Potassium hydroxide (58.76 gm), copper acetate (7.6 gm) and ethylene diamine (3.34 gm) were added and the contents heated at 120° C. (100-150° C.) for 16 hours (10-20 hours). The contents were brought to room temperature and diluted with water (1950 ml) and extracted with hexane (2×800 ml). The organic layer was washed with water (2×650 ml), brine (650 ml), dried over anhydrous sodium sulphate. The organic layer was treated with carbon, and solvent was removed under reduced pressure. Crude product was dissolved in toluene (325.0 ml) and 1-chloroethylchloroformate (59.8 gm) was added drop wise over a period of 10 minutes. The mixture was heated at 90° C. (80-120° C.) for 3 hours (2-6 hours) after which the solvent was removed under reduced pressure. Methanol (325.0 ml) was added and the contents heated at 70° C. (50-80° C.) for 2 hours (2-8 hours). The contents were allowed to cool to room temperature and solvent removed under reduced pressure. The crude was stripped with acetone (3×65 ml). The compound was isolated in acetone (325.0 ml) as solid (35.0 gm).

Example 5: Preparation of 1-(2-((2,4-dimethylphenyl)thio)phenyl)piperazine HBr 1-(2-((2,4-dimethylphenyl)thio)phenyl)piperazine hydrochloride (100 gm) was dissolved in ethyl acetate (1000 ml) and water (1000 ml) and the reaction mass pH adjusted to 8.0-9.0 with 10% sodium hydroxide solution at 25-35° C., and both layers were separated. The organic layer was washed with water (2×500 ml), organic layer treated with carbon; slowly added aqueous hydrobromic acid into the organic layer. The reaction mass was maintained 2 hours and the compound filtered, the wet compound was taken in methanol (600 ml), heated to reflux, further cooled to 25-35° C., and filtered the pure titled compound (75 gm).

Example 6: Preparation of Vortioxetine Hydrobromide Propylene Glycol Solvate Form AC1

Vortioxetine hydrobromide (10 g) and propylene glycol (30 ml) were charged into a round bottom flask and heated to 90-95° C. to obtain a clear solution. The resulting reaction solution was maintained at the same temperature for about 1.0 hour. The obtained clear solution was cooled to 20-30° C. and stirred for 30 minutes. Further cooled to 0-5° C. and stirred it for 12 hrs. Raised temperature 20-30° C. and stirred for 2.0 hrs. The obtained solid was filtered and washed with propylene glycol 5 ml, suction dried, dried in a vacuum tray dried for about 24 hours to obtain vortioxetine hydrobromide propylene glycol solvate form AC1.

Although the compounds, schemes and methods of the present disclosure have been described with reference to exemplary embodiments thereof, the present disclosure is not limited thereby. Indeed, the exemplary embodiments are implementations of the disclosed methods are provided for illustrative and non-limitative purposes. Changes, modifications, enhancements and/or refinements to the disclosed methods may be made without departing from the spirit or scope of the present disclosure. Accordingly, such changes, modifications, enhancements and/or refinements are encompassed within the scope of the present invention. All publications, patent applications, patents, figures and other references mentioned herein are expressly incorporated by reference in their entirety.

What is claimed is:

1. A process for preparing vortioxetine hydrobromide propylene glycol solvate form AC1 comprising the steps of:
    a. combining vortioxetine hydrobromide and propylene glycol to obtain a solution of vortioxetine hydrobromide in propylene glycol;
    b. maintaining the solution of step a) at a temperature of about 0° C. to about 150° C.; and
    c. isolating vortioxetine hydrobromide propylene glycol solvate form AC1.

2. Crystalline vortioxetine hydrobromide propylene glycol solvate form AC1 characterized by data selected from: an x-ray powder diffraction pattern with peaks at about 19.82, 20.97, 23.06, 25.7, 29.77±0.2 degrees 2-theta; an x-ray powder diffraction pattern with peaks substantially as depicted in FIG. 1; or a combination thereof.

3. Crystalline vortioxetine hydrobromide propylene glycol solvate form AC1 characterized by an x-ray powder diffraction pattern with peaks at about 19.64, 22.85, 25.51, 29.57, 30.18±0.2 degrees 2-theta.

4. Crystalline vortioxetine hydrobromide propylene glycol solvate form AC1 characterized by an x-ray powder diffraction pattern with peaks substantially as depicted in FIG. 3.

* * * * *